United States Patent
Woo et al.

(10) Patent No.: US 7,847,565 B2
(45) Date of Patent: Dec. 7, 2010

(54) SYSTEM FOR ELECTRICAL IMPEDANCE TOMOGRAPHY AND METHOD THEREOF

(75) Inventors: Eung Je Woo, Seongnam-si (KR); Dong In Oh, Yongin-si (KR); Jin Keun Seo, Seoul (KR); Oh In Kwon, Seoul (KR)

(73) Assignee: University-Industry Cooperation Group of Kyunghee University, Yongin (KR)

( * ) Notice: Subject to any disclaimer, the term of this patent is extended or adjusted under 35 U.S.C. 154(b) by 306 days.

(21) Appl. No.: 12/088,685

(22) PCT Filed: Jul. 28, 2006

(86) PCT No.: PCT/KR2006/002977

§ 371 (c)(1),
(2), (4) Date: Mar. 29, 2008

(87) PCT Pub. No.: WO2007/089062

PCT Pub. Date: Aug. 9, 2007

(65) Prior Publication Data

US 2008/0252304 A1 Oct. 16, 2008

(30) Foreign Application Priority Data

Feb. 3, 2006 (KR) .................. 10-2006-0010629

(51) Int. Cl.
*G01R 27/08* (2006.01)

(52) U.S. Cl. .............. 324/692; 324/713; 600/547
(58) Field of Classification Search ............. 324/692, 324/713
See application file for complete search history.

(56) References Cited

U.S. PATENT DOCUMENTS

| 5,311,878 | A | 5/1994 | Brown |
| 5,626,146 | A | 5/1997 | Barber |
| 2004/0242989 | A1* | 12/2004 | Zhu et al. .................. 600/407 |

* cited by examiner

*Primary Examiner*—Vincent Q Nguyen
(74) *Attorney, Agent, or Firm*—Workman Nydegger

(57) ABSTRACT

A system for electrical impedance tomography and method thereof are disclosed, by which electrical characteristics within a measurement target can be precisely detected. The present invention includes the steps of injection a current to a measurement target via at least one electrode pair selected form a plurality of electrodes (250) attached to the measurement target, detecting voltage of a surface of the measurement target using a plurality of voltmeters (260) connected to the electrodes that are not selected, respectively, adjusting gains of the voltmeters according to maximum values of the detected voltages, respectively, amplifying the detected voltages using the gain-adjusted voltmeters, respectively, and imaging an internal part of the measurement target based on the amplified voltages.

15 Claims, 4 Drawing Sheets

SYSTEM FOR ELECTRICAL IMPEDANCE TOMOGRAPHY AND METHOD THEREOF

TECHNICAL FIELD

The present invention relates to a medical instrument, and more particularly, to a system for electrical impedance tomography and method thereof. Although the present invention is suitable for a wide scope of applications, it is particularly suitable for detecting an electrical characteristic within a measurement target precisely.

BACKGROUND ART

Generally, X-rays, MRI, ultrasonic waves and the like are used in imaging an internal structure of a human body or object. Specifically, in order to image electrical characteristics of a human body or object, many efforts have been made to image a current density within a measurement target using an MRI technique.

As a technique for imaging electrical characteristics of a human body or object, there is EIT (electrical impedance tomography) having been actively researched and studied since 1970's.

The EIT technology provides a resistivity or conductivity image indicating electrical characteristics of a measurement target. By mainly targeting a human body as a measurement object, the EIT technology images conductivity within the human body in a manner of attaching a plurality of electrodes to a surface of the human body. In particular, after a current has been applied via a plurality of the electrodes attached to the surface of the human body, the conductivity within the human body is imaged by measuring voltages via the electrodes. Thus, the internal part of the human body can be imaged according to the conductivity. This is because living organs including blood, bones, lungs, heart and the like differ from one another in electrical characteristics.

However, in case of measuring a voltage of a human body using the related art EIT technique and instrument, the measured voltage contains various kinds of noises. Since these noises make it difficult to precisely detect the electrical characteristics of various organs of the human body, it is unable to precisely image the internal part of the human body.

Moreover, the conventional EIT instrument includes too many devices, whereby its configuration is considerably complicated. Hence, the conventional EIT instrument has a considerably large size and a high product cost.

DISCLOSURE OF THE INVENTION

Accordingly, the present invention is directed to a system for electrical impedance tomography and method thereof that substantially obviate one or more of the problems due to limitations and disadvantages of the related art.

An object of the present invention is to provide a system for electrical impedance tomography and method thereof, by which electrical characteristics within a measurement target can be precisely detected.

Additional features and advantages of the invention will be set forth in the description which follows, and in part will be apparent from the description, or may be learned by practice of the invention. The objectives and other advantages of the invention will be realized and attained by the structure particularly pointed out in the written description and claims thereof as well as the appended drawings.

To achieve these and other advantages and in accordance with the purpose of the present invention, as embodied and broadly described, a method of electrical impedance tomography according to the present invention includes the steps of injecting a current to a measurement target via at least one electrode pair selected from a plurality of electrodes attached to the measurement target, detecting voltage of a surface of the measurement target using a plurality of voltmeters connected to the electrodes that are not selected, respectively, adjusting gains of the voltmeters according to maximum values of the detected voltages, respectively, amplifying the detected voltages using the gain-adjusted voltmeters, respectively, and imaging an internal part of the measurement target based on the amplified voltages.

To further achieve these and other advantages and in accordance with the purpose of the present invention, a system for electrical impedance tomography includes a plurality of electrodes attached to a measurement target for current injection and voltage detection, a current source supplying a current to a plurality of the electrodes, a board including a plurality of switches to selectively provide the current to at least one selected electrode pair from the current source, a plurality of voltmeters detecting voltages of a surface of the measurement target via the electrodes not selected, the voltmeters amplifying the detected voltages after adjusting amplification rates of the detected voltages according to maximum values of the detected voltages, and a main controller imaging an internal part of the measurement target based on the amplified voltages.

It is to be understood that both the foregoing general description and the following detailed description are exemplary and explanatory and are intended to provide further explanation of the invention as claimed.

BRIEF DESCRIPTION OF DRAWINGS

The accompanying drawings, which are included to provide a further understanding of the invention and are incorporated in and constitute a part of this specification, illustrate embodiments of the invention and together with the description serve to explain the principles of the invention.

In the drawings.

BEST MODE FOR CARRYING OUT THE INVENTION

Reference will now be made in detail to the preferred embodiments of the present invention, examples of which are illustrated in the accompanying drawings.

First of all, electrical impedance tomography (hereinafter abbreviated EIT) is able to image a conductivity distribution within a measurement target such as a human body, an animal and the like. An electrical impedance tomograph measures boundary voltages on a surface of a human body by injecting a current into a human body using a plurality of electrodes attached to a circumference of a measurement target, e.g., a chest circumference of the human body. The electrical impedance tomograph then generates a conductivity distribution image based on the measured boundary voltages.

The present invention proposes two kinds of electrical impedance tomography methods. A first type is to provide a current to a measurement target via an electrode pair randomly selected from one current source. And, a second type uses a plurality of current sources each of which injects a current to a measurement target via a designated electrode. In this case, a total sum of currents coming from all active current sources is always zero.

In an EIT system according to the present invention capable of implementing the two kinds of the electrical impedance tomography methods, voltages from all or selected electrodes are simultaneously measured by a plurality of voltmeters connected parallel to one another.

Figure 1:
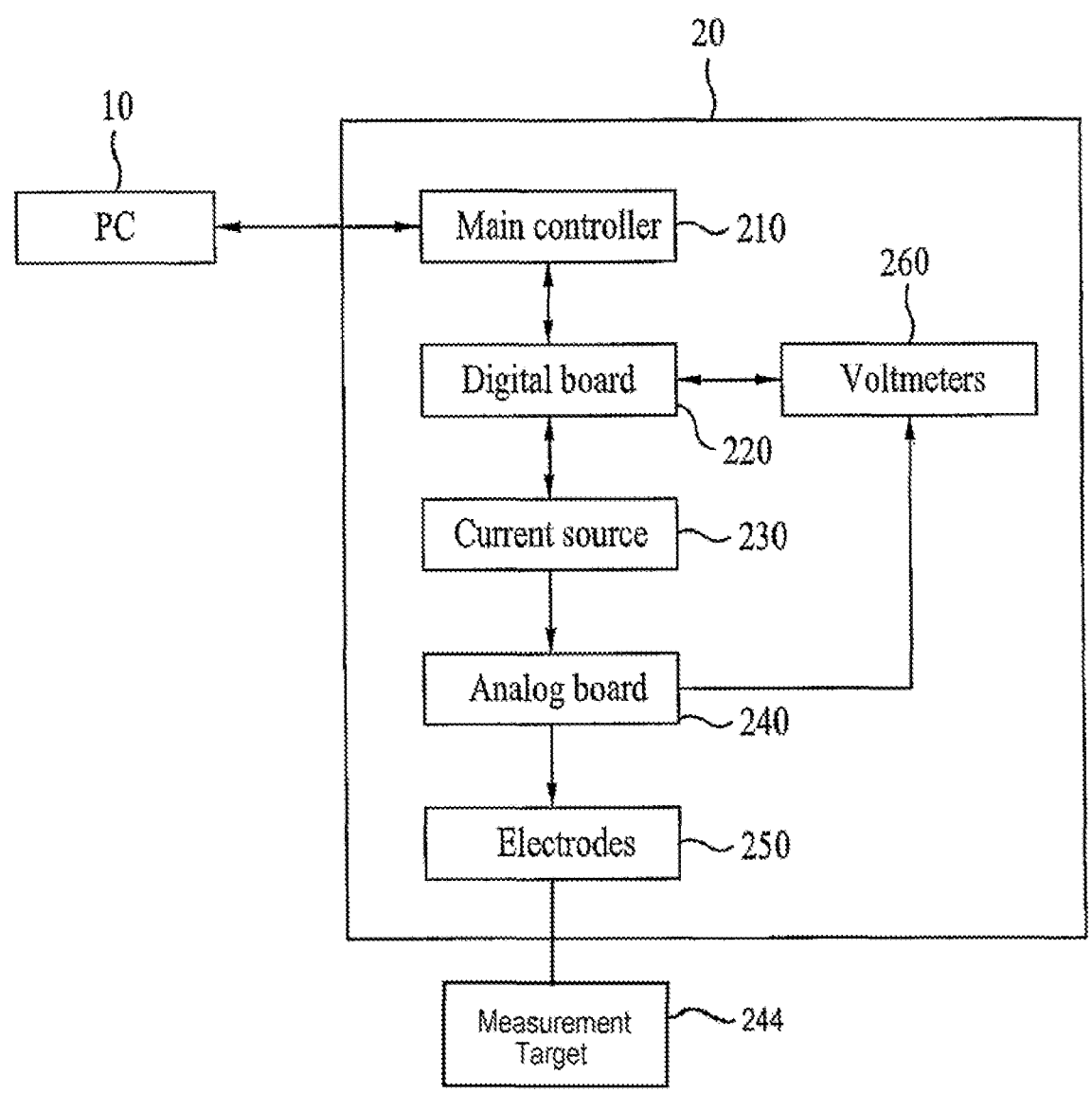
FIG. 1 is a block diagram of an EIT system according to one embodiment of the present invention.

FIG. 1 is a block diagram of an EIT system according to one embodiment of the present invention.

Referring to FIG. 1, an EIT system 20 according to one embodiment of the present invention includes a main controller 210 having a USB interface to communicate with a PC 10, a digital motherboard (or digital backplane) 220 including an intra-network controller, a balanced current source 230 including a calibrator, an analog motherboard (or analog backplane) 240 including a switching circuit, a plurality of electrodes 250 detecting a voltage of a measurement target 244 by injecting a current into the measurement target 244 and a plurality of voltmeters (voltage measuring unit) 260 electrically connected to the analog motherboard 240 and the digital motherboard 220, respectively.

The PC 10 controls all functions of the EIT system 20 via the main controller 210 connected by the USB interface. The PC 10 having a USB port can be used as a console or a user interface device of the EIT system 20. The PC 10 exchanges a command and data with the main controller 210 via the USB port. The command is transported as a packet of maximum 10 bytes. The PC 10 includes EIT software.

A wire or wireless data link is used for a connection between the PC 10 and the EIT system 20. In case of a wire connection, a standard USB cable having a USB optical separator is used. In case of a wireless RF connection, an order-type design USB card using a USB controller is used. The USB controller interfaces with a 2.4 GHz RF serial communication module having an antenna.

In case of receiving a command from the PC 10, the main controller 210 controls all functions of the EIT system to collect boundary voltage data of a measurement target. For instance, the main controller 210 selects a frequency and channel according to the command of the PC 10. To select a channel, the main controller 210 sets up a current injection electrode 250 and a voltage detection electrode 250.

The main controller 210 controls the current injection electrode to inject a current into the measurement target and the voltage detection electrode to detect a voltage of the measurement target.

The main controller 210 collects channel information (ID), gain information and the like of the voltmeters 260 as well as the detected voltage. The collected data are transferred to the PC 10.

The main controller provides 40 MHz clock signal for synchronization between the current source 230 and the voltmeters 260.

The main controller 210 includes a USB controller to communicate with the PC 10. The USB controller can be directly connected to the PC 10 by 2 Mbps via a USB optical separator. Alternatively, in the wireless RF connection, the USB controller interfaces with a 2.4 GHz serial communication module by 1 Mbps.

A data link between the main controller 210 and the current source 230 or between the main controller 210 and the voltmeters 260 is called an intra-network and is based on a half-duplex high-speed synchronous serial data communication channel. This data communication channel is controlled by two FPGAs (field-programmable gate array) integrated circuits on the digital motherboard 220, i.e., an intra-network controller. This serial intra-network can be used in removing a digital bus propagating digital clock noise via a system.

The digital motherboard 220 is placed under the main controller 210 and exchanges address, data and control signals with the main controller via two 34-pin connectors. The intra-network controller located in the middle of the digital motherboard 220 is implemented into two FPGA forms. The intra-network controller controls command and data transmissions between the main controller 210 and other elements. The intra-network controller includes total nine half-duplex sync serial ports each of which has 10 Mbps data rate. Each of the serial ports is responsible for eight voltmeters 260 using time division multiplexing implemented by the same FPGA. A digital control signal and DC power for each of the voltmeters 260 are provided to the corresponding voltmeter 260 via a plurality of 6-pin connectors radially arranged on an outer circumference of the digital motherboard 220.

The current source 230 is placed under the digital motherboard 220 and is connected to the digital motherboard 220 via eight 4-pin connectors to receive a clock signal and to transmit a sync signal.

The current source 230 is placed on the analog motherboard 240 and M connectors arranged along an outer circumference of the current source 230 are connected to connectors of the analog motherboard 240.

Figure 2:
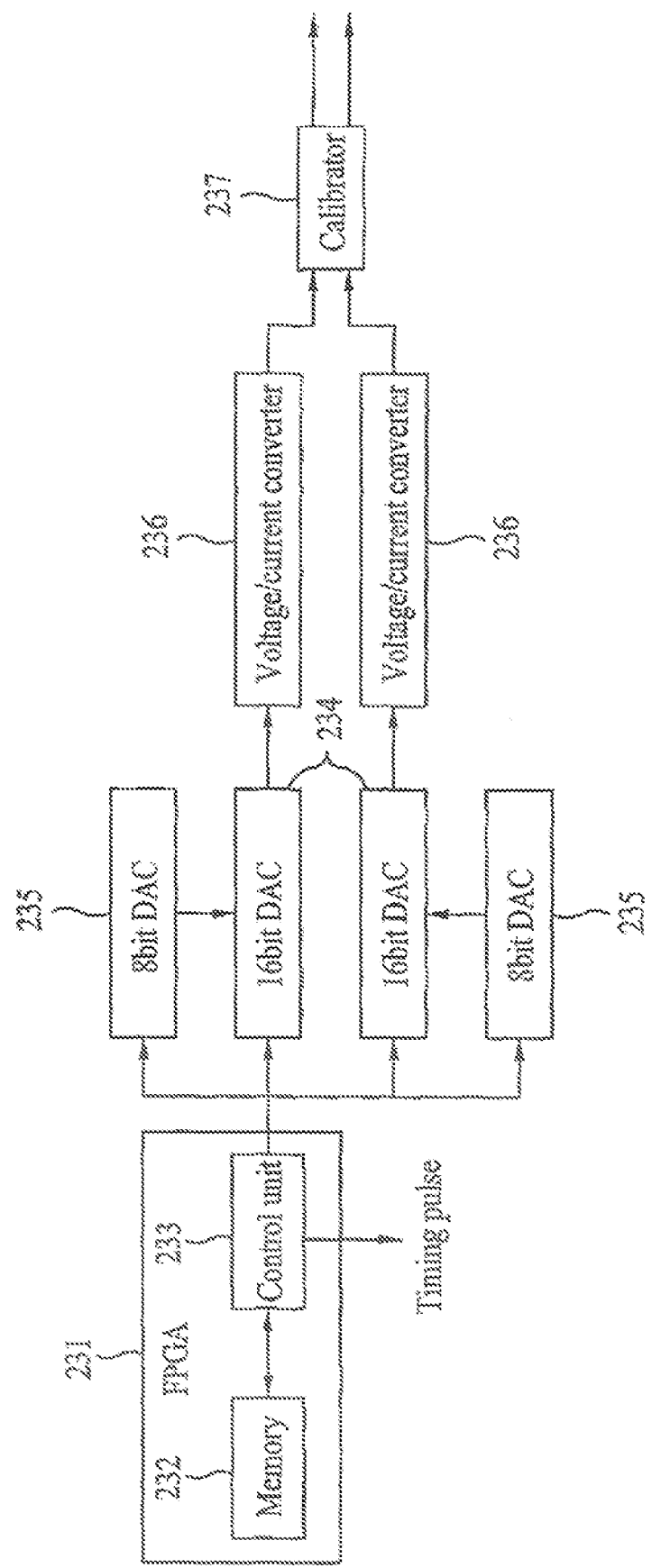
FIG. 2 is a schematic block diagram of a current source.

FIG. 2 is a schematic block diagram of a current source.

Referring to FIG. 2, the current source 230 includes an FPGA (or integrated circuit) 231, a 16-bit D/A (digital/analog) converter 234, an 8-bit D/A converter 235, a voltage-to-current converter 236 and a calibrator (or impedance converter) 237.

The FPGA 231 includes a memory 232 storing 16-bit data of a normalized sine wave having a ¼ cycle transferred from the main controller 210 and a control unit 233 adjusting a frequency of the sine wave. And, the FPGA 231 further includes a serial port (not shown in the drawing) for an intra-network connection, a digital waveform generator and an address generator outputting 16-bit data.

The control unit 233 adjusts the frequency of the sine wave using the address generator. For instance, the control unit 233 is able to select a frequency having a range between 10 Hz and 500 KHz.

The control unit 233 is able to adjust an amplitude of a voltage signal outputted from the 16-bit D/A converter 234 by controlling an output of the 8-bit D/A converter 235. Hence, the current source 230 generates a voltage signal having a variable amplitude and frequency.

And, the control unit 233 outputs a sync pulse when each sine wave cycle begins. The outputted sync pulse, which is a timing pulse, is transferred to the whole voltmeters 260 via the digital motherboard 220.

A voltage signal from the 16-bit D/A converter 234 is converted to a current by the voltage-to-current converter 236. In this case, a current pump circuit can be used as the voltage-to-current converter 236.

The calibrator 237 includes two digital potentiometers (variable resistors) to maximize an output impedance of the current source 230. One of the two digital potentiometers is used in balancing resistance values of the two voltage-to-current converters 236, while the other is used in erasing stray capacitances from outputs of the two voltage-to-current converters 236. The resistance values of the voltage-to-current converters 236 are balanced to supply a same current to each of the two selected electrodes 250. In the present invention, the current source 230 is designed to have 64 MΩ output impedance. An output of the current source 230 is transferred to a pair of the selected electrodes 250 via a switching network of the analog motherboard 240 that uses a T-bar switch.

The EIT system has 64 voltmeters and 64 electrodes in one example.

A plurality of the voltmeters 260, e.g., 8, 16, 32 or 64 voltmeters are connected to the digital motherboard 220 and the analog motherboard 240, respectively and arranged in a radial form. The voltmeter 260 can be connected to the electrode 250 one-on-one via a switch of the analog motherboard 240.

Figure 3:
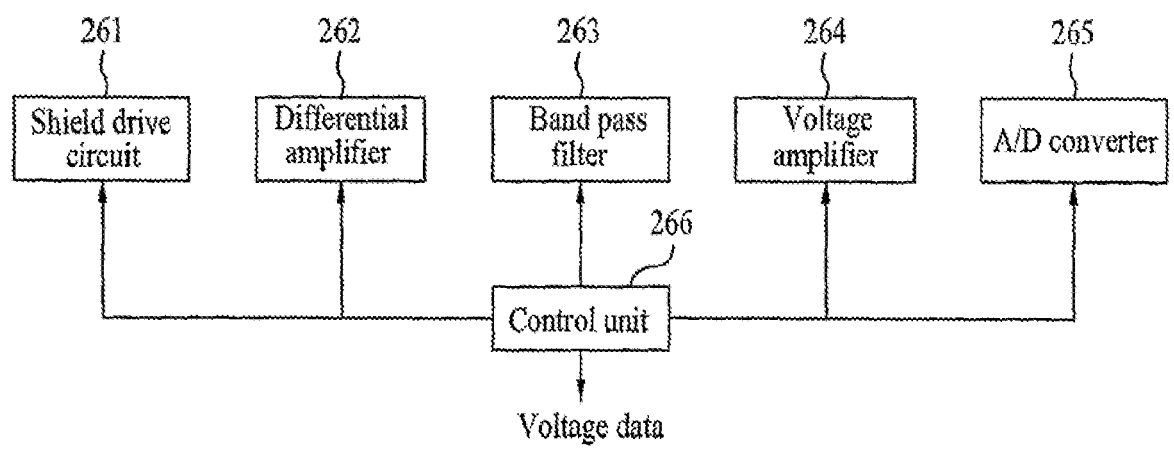
FIG. 3 is a schematic block diagram of a voltmeter.

FIG. 3 is a schematic block diagram of a voltmeter.

Referring to FIG. 3, the voltmeter 260 includes a Active shield drive circuit 261, a differential amplifier 262, a band pass filter 263, a voltage amplifier 264, an A/C (analog-to-digital) converter 265 and a control unit 266.

The Active shield drive circuit 261 receives a voltage detected by the corresponding electrode 250 according to a command of the control unit 266.

The differential amplifier 262 has a fixed gain of '1' to convert a differential voltage between a pair of the neighbor electrodes 250 to a single-ended signal.

A signal outputted from the differential amplifier 262 undergoes band pass filtering through the band pass filter 263 and is then provided to the voltage amplifier 264 having a variable gain.

The voltage amplifier 264 includes a digital potentiometer having a maximum gain of '2,500'.

A signal amplified by the voltage amplifier 264 is digitized by the 12-bit A/D converter with a 10 MHz sampling frequency according to a non-uniform sampling technique.

The non-uniform sampling technique means that a sampling is performed with a different timing each cycle of the amplified signal. For instance, assuming that one cycle of a signal is '1', the signal is sampled each 0.1, 0.3. 0.5, 0.7 and 0.9 cycle during an odd cycle or each 0.2, 0.4, 0.6, 0.8 or 1.0 cycle during an even cycle.

The control unit 266 is configured in an FPGA form. The control unit 266 includes an infra-network half-duplex sync type serial port, a spike noise removing digital filter, an auto-gain controller and a digital phase-sensitive demodulator.

The control unit 266 calculates a slope of voltage data continuously outputted from the A/D converter 265. If the calculated slope exceeds a threshold, the control unit 266 decides that noise is included in the corresponding voltage data. The control unit 266 then replaces the corresponding voltage data by a new value.

Figure 4:
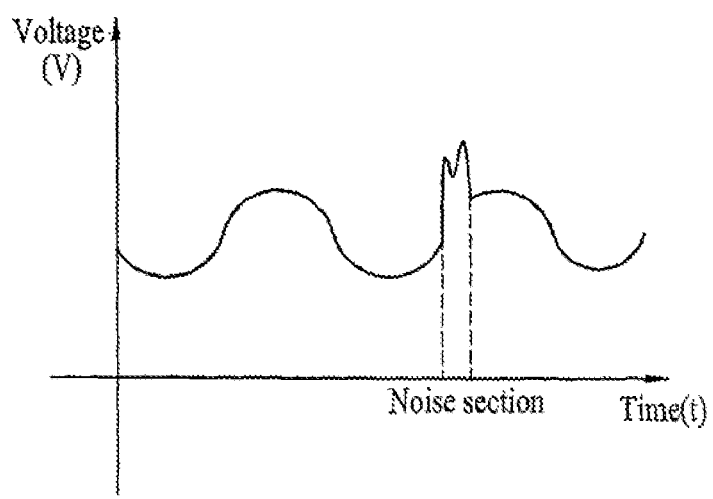
FIG. 4 is a graph of voltage data including noise.

For instance, a shown in FIG. 4, if noise is included in the voltage data, the voltage data corresponding to the noise section is replaced by another value. The replacement value is an ideal voltage value estimated based on a current value supplied to the electrode 250.

The control unit 266 detects a peak value of the voltage data for one cycle of a sine wave outputted from the main controller 210.

The control unit 266 adjusts a gain of the voltage amplifier 264 in a range between 1~2,500 to have the detected peak value reach 90% of the maximum output of the A/D converter 265.

And, the control unit 266 controls a variable resistor included in the voltage amplifier 264 to adjust a gain (or amplification rate) of the voltage amplifier 264.

In the present invention, the voltmeter 260 is designed to have 104 dB SNR (signal to noise ratio) by appropriately selecting the number of data samples required for a signal average.

The analog motherboard 240 includes a plurality of switches 242 to provide injection current to a pair of the selected electrodes 250.

The entire pairs of the electrodes 250 used for current injection have the same signal path length from the current source 230.

The current source 230 and the digital motherboard 220 are stacked over the analog motherboard, and the entire voltmeters 260 are plugged in the analog motherboard 240 and the digital motherboard 220 in a radially symmetric form.

The analog motherboard 240 includes a routing path for the voltmeter 260 from an electrode connector.

The analog motherboard 240 is placed under the current source 230 and connected to connectors of the current source 230.

The analog motherboard 240 includes M connectors connected to M connectors of the voltmeters 260, respectively.

The analog motherboard 240 includes switches to route an injected current to a pair of the selected electrodes 250. Some switches make the selected electrode 250 short-circuited temporarily to discharge storage charges remaining within the measurement target due to a previous current injection.

The analog motherboard 240 includes a plurality of current detecting resistors. An injected current passes a current flow path and current detecting resistors arranged in serial. The current detecting resistors are able to measure a current by detecting a voltage difference between resistors instead of a general voltage difference between two neighbor electrodes. And, a surface voltage of the measurement target is compensated based on the current measured by the current detecting resistors.

For instance, if an actually inject current is 0.99 mA despite a requirement of 1 mA, a value of the surface voltage is increased to a level induced by the current of 1 mA.

A different T-bar switch is used in connecting the voltmeter to a pair of neighbor electrodes or one of two terminals of the current detecting resistor. Theses switches are controlled by the FPGA within each of the voltmeters 260 based on a command from the main controller 210.

Figure 5:
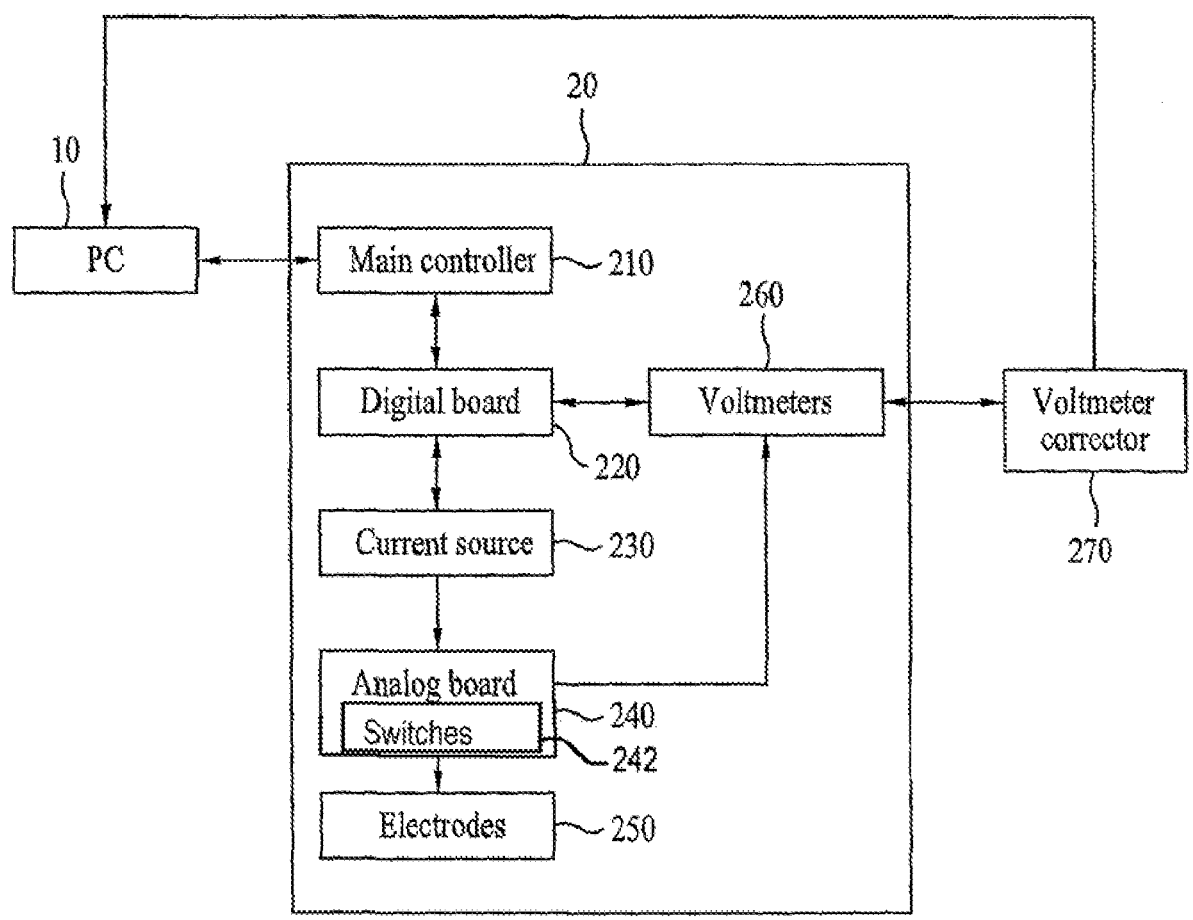
FIG. 5 is a block diagram of an EIT system including a voltmeter calibrator according to the present invention.

FIG. 5 is a block diagram of an EIT system including a voltmeter calibrator according to the present invention.

Referring to FIG. 5, the present invention includes a voltmeter corrector 270 to calibrate errors attributed to gain and frequency differences of each of the voltmeters 260.

The voltmeter corrector 270 includes an intra-channel calibrator correcting a gain difference between the voltmeters 260 and an inter-channel calibrator (resistor phantom) calibrating the voltmeter 260 not to output a different value according to a frequency.

In the present invention, 31 different gains are generally used among total 65,536 available gains. And, ten frequencies are selected from 4,096 available frequencies within a range between 10 Hz~500 KHz.

So, after the intra-channel calibration by the intra-channel calibrator, a 3-dimensional table of a number having a 31*10*64 size corresponding to a case that there are sixty-four voltmeters 260 is generated.

The voltmeter corrector 270 is connected to the PC 10 via a USB port and the PC 10 automatically controls a calibration sequence. Intra-channel calibration software, which is being executed in the PC 10, stores a calibration table in a hard disc for a continuous use for real-time calibration of voltage data from each channel.

Features of the voltmeters 260 cannot be identical to one another due to various reasons. To compensate variations of parameters of each of the voltmeters 260 (i.e., to compensate an inter-channel variation), the present invention proposes an inter-channel calibrator.

A resistance of the calibrator can be precisely measured using a high-precision digital multi-meter. A set of boundary voltage data for all injected currents is measured using all cables connected to the inter-channel calibrator.

An amplitude and phase of the measure voltage data are compares to ideal values that are numerically calculated. This generates a scaling factor of a complex number for each voltage data in the voltage data set.

An inter-channel calibration table including all theses complex numbers is stored in the PC 10 for real-time calibration.

The present invention proposes a cylindrical 2-dimensional saline phantom having a 200 mm diameter and a 100 mm height. This phantom is filled with saline having 0.44 S/m conductivity.

A method of electrical impedance tomography according to the present invention is explained as follows.

First of all, if the main controller 210 receives a command for imaging a measurement target from the PC 10, the main controller 210 selects a channel and a frequency of a sine wave according to the command of the PC 10. In this case, the main controller 210 selects a pair of electrodes 250 corresponding to the selected channel. A pair of the selected electrodes 250 is used in injecting a current into the measurement target, whereas the rest of the electrodes 250 that are not selected are used in measuring a surface voltage of the measurement target.

And, the main controller 210 outputs a 40 MHz clock signal for the synchronization of the current source 230 and the voltmeters 260.

Once the channel and the frequency of the sine wave are selected, the main controller 210 outputs a control signal for controlling the current source 230 via the digital motherboard 220. In this case, the control signal includes information for the selected frequency.

The FPGA 231 of the current source 230 receives and stores the control signal from the main controller 210 and then generates a sine wave voltage signal based on the received control signal. In particular, the FPGA 231 generates the voltage signal based on the frequency information included in the control signal and then transfers the generated voltage signal to the two 16-bit D/A converters 234. In doing so, the FPGA 231 controls the 8-bit D/A converter 235 to adjust an amplitude of the voltage signal transferred to the 16-bit D/A converters 234.

Subsequently, voltage signals outputted from the two 16-bit D/A converters 234 are converted to two currents by the voltage-to-current converters 236, respectively. The two currents are then transferred to the calibrator 237.

The calibrator 237 adjusts the two currents to make identical in amplitude and frequency. In this case, there exists a 180° phase difference between the two currents.

Besides, the main controller 210 turns on switches of the analog motherboard 240 corresponding to the selected electrodes 250 so that the two currents having passed through the calibrator 237 can be transferred to the two selected electrodes 250, respectively. If so, the two currents are injected into the measurement target via the two selected electrodes 250.

The current injected into the measurement target induces a voltage differing in level on a surface of the measurement target according to a resistivity or conductivity difference between internal tissues of the measurement target.

If the unselected electrodes 250 detect the voltage on the surface of the measurement target, the voltmeters 260 corresponding to the unselected electrodes 250 receives the surface voltage detected by the electrode 250 via the analog motherboard 240.

The control unit 266 of each of the voltmeters 266 decides whether noise is included in the surface voltage data based on the slope of the detected surface voltage data. If the noise is included in the surface voltage data, the control unit 266 replaces the corresponding voltage data by a different voltage value.

The control unit 266 adjusts a gain of the voltage amplifier 264 according to a maximum value of the voltage data. For instance, if the maximum value of the voltage data reaches 90% of a maximum output of the A/D converter 265, the control unit 266 does not adjust the gain of the voltage amplifier 264. If the maximum value of the voltage data does not reach 90% of a maximum output of the A/D converter 265, the control unit 266 increases the gain of the voltage amplifier 264.

If the noise is removed from the voltage data and if the gain of the voltage amplifier 264 is adjusted, the voltage amplifier 264 amplifies the voltage data according to the adjusted gain value and the A/V converter 265 converts voltage data outputted from the voltage amplifier 264 to a digital value.

Subsequently, each of the control units 266 transfers the digitized voltage data to the main controller 210 via the digital motherboard 220 together with channel information and gain information. In this case, the channel information includes an ID or number indicating the corresponding voltmeter 260 and the gain information includes a gain value adjusted by the control unit 266.

The main controller 210 collects the channel information, the gain information and the voltage data transferred from the voltmeters 260 and then transfers the collected information and voltage data to the PC 10. While collecting the channel information, the gain information and the voltage data, the main controller 210 controls the selected electrodes 250 to discharge the storage charges remaining within the measurement target.

The PC 10 receives the channel information, the gain information and the voltage data from the main controller 210 and then stores the per-channel gain information and voltage data per channel in a storage medium such as a hard disc and the like.

The PC 10 processes the voltage data by considering the per-channel gain information. If the detected voltage data is used as it is, since gain values of the voltmeters 260 are different from each other, it is difficult to represent electrical characteristics within the measurement target. So, the corresponding voltage value should be decreased or increased according to the gain value of each of the voltmeters 260. For instance, if the gain value of the voltmeter 260 is greater than a reference gain value, the corresponding voltage value is decreased. Alternatively, a rate of the gain value of the voltmeter 260 over the reference gain value is multiplied by the corresponding voltage value.

After having processed the voltage data by considering the per-channel gain information, the PC 10 images an internal part of the measurement target using the voltage data. In this case, various methods for imaging the internal part of the measurement target can be applied using the voltage data of the surface of the measurement target.

INDUSTRIAL APPLICABILITY

Accordingly, the present invention provides the following effects or advantages.

First of all, an analog motherboard is separated from a digital motherboard and voltmeters connected to the digital and analog motherboards are arranged radially and symmetrically. Hence, the present invention is able to considerably reduce digital clock noise.

Secondly, the present invention uses a plurality of electrodes and a plurality of voltmeters. Since each of the voltmeters is able to remove spike noise and adjust a gain automatically, precise voltage data of a measurement target can be obtained.

While the present invention has been described and illustrated herein with reference to the preferred embodiments thereof, it will be apparent to those skilled in the art that various modifications and variations can be made therein without departing from the spirit and scope of the invention. Thus, it is intended that the present invention covers the modifications and variations of this invention that come within the scope of the appended claims and their equivalents.

The invention claimed is:

1. A method of electrical impedance tomography, injecting the at least one comprising the steps of:
    injecting a current to a measurement target via at least one electrode pair selected from a plurality of electrodes attached to the measurement target;
    detecting voltage of a surface of the measurement target using a plurality of voltmeters connected to the electrodes that are not selected, respectively;
    removing noise included in the detected voltages based on slopes of the detected voltages;
    adjusting gains of the voltmeters according to maximum values of the detected voltages, respectively;
    amplifying the detected voltages using the gain-adjusted voltmeters, respectively; and
    imaging an internal part of the measurement target based on the amplified voltages.

2. The method of claim 1, the step of injecting the current to the measurement target via the at least one selected electrode pair, comprising the steps of
    selecting the electrode pair and a frequency;
    generating a voltage signal according to the selected frequency;
    converting the voltage signal to a current; and
    injecting the current into the measurement target via the selected electrode pair.

3. The method of claim 1, the step of injecting the current to the measurement target via the at least one selected electrode pair, comprising the steps of
    converting a voltage signal to two currents differing in phase;
    calibrating the two currents to have a same amplitude and frequency; and
    injecting the two currents into the measurement target via the selected electrode pair, respectively.

4. The method of claim 1, wherein if the slope of the detected voltage exceeds a threshold, a voltage of a section corresponding to the slope exceeding the threshold is replaced by a preset voltage value.

5. The method of claim 1, the step of adjusting the gains of the voltmeters according to the maximum values of the detected voltages, respectively, comprising the step of adjusting the gains of the voltmeters to have the maximum values of the detected voltages equal to or greater than 90% of maximum outputs of the voltmeters, respectively.

6. The method of claim 1, the step of imaging the internal part of the measurement target based on the amplified voltages, comprising the steps of:
    adjusting sizes of the amplified voltages according to gain values of the voltmeters, respectively; and
    imaging the internal part of the measurement target based on the adjusted voltage sizes.

7. A system for electrical impedance tomography, comprising:
    a plurality of electrodes attached to a measurement target for current injection and voltage detection;
    a current source supplying a current to a plurality of the electrodes;
    a board including a plurality of switches to selectively provide the current to at least one selected electrode pair from the current source;
    a plurality of voltmeters detecting voltages of a surface of the measurement target via the electrodes not selected, the voltmeters removing noises included in the detected voltages based on slopes of the detected voltages, respectively, and the voltmeters amplifying the detected voltages after adjusting amplification rates of the detected voltages according to maximum values of the detected voltages; and
    a main controller imaging an internal part of the measurement target based on the amplified voltages.

8. The system of claim 7, the current source comprising:
    a control unit outputting a digital voltage signal according to a command of the main controller;
    a pair of first D/A converters converting the digital voltage signal to two analog voltage signals, respectively;
    a pair of second D/A converters adjusting amplitudes of the two analog voltage signals, respectively;
    a pair of voltage-to-current converter converting the two analog voltage signals to two currents, respectively; and
    a calibrator calibrating the two currents outputted from the voltage-to-current converter to make the two calibrated currents identical to each other in amplitude and frequency and maximizing of the output impedance of two current sources.

9. The system of claim 7, each of a plurality of the voltmeters, comprising:
    a voltage amplifier amplifying the corresponding detected voltage;
    an A/D converter converting the amplified voltage to digital voltage data; and
    a control unit adjusting a gain of the voltage amplifier.

10. The system of claim 9, wherein the A/D converter samples the amplified voltage by a non-uniform sampling technique.

11. The system of claim 7, wherein each of a plurality of the voltmeters transmits an ID, the adjusted amplification rate and the detected voltage to the main controller.

12. The system of claim 7, wherein if the slope of the detected voltage exceeds a threshold, the corresponding voltmeter replaces a voltage of a section corresponding to the slope exceeding the threshold by a preset voltage value.

13. The system of claim 7, wherein the main controller controls the selected electrode pair to discharge storage charges remaining within the measurement target while collecting the amplification rates of the voltmeters and the detected voltages.

14. The system of claim 7, wherein a plurality of the voltmeters are arranged radially and symmetrically.

15. The system of claim 7, further comprising a motherboard controlling a network between the current source, the board, the voltmeters and the main controller.

* * * * *